(12) United States Patent
Takahashi et al.

(10) Patent No.: US 11,789,013 B2
(45) Date of Patent: *Oct. 17, 2023

(54) COMPONENTIAL ANALYZER, DRUG EFFICACY ANALYZER, AND ANALYSIS METHOD

(71) Applicant: Hitachi High-Tech Corporation, Tokyo (JP)

(72) Inventors: Ryosuke Takahashi, Tokyo (JP); Katsuhiro Kanda, Tokyo (JP); Yusuke Shimizu, Tokyo (JP); Hisashi Ichikawa, Tokyo (JP)

(73) Assignee: Hitachi High-Tech Corporation, Tokyo (JP)

(*) Notice: Subject to any disclaimer, the term of this patent is extended or adjusted under 35 U.S.C. 154(b) by 646 days.

This patent is subject to a terminal disclaimer.

(21) Appl. No.: 16/856,459

(22) Filed: Apr. 23, 2020

(65) Prior Publication Data
US 2020/0249223 A1 Aug. 6, 2020

Related U.S. Application Data

(63) Continuation of application No. 15/847,092, filed on Dec. 19, 2017, now Pat. No. 10,684,276, which is a (Continued)

(30) Foreign Application Priority Data

Nov. 29, 2013 (JP) ................................. 2013-246906

(51) Int. Cl.
*G01N 33/50* (2006.01)
*G01N 35/10* (2006.01)
(Continued)

(52) U.S. Cl.
CPC ............ *G01N 33/5067* (2013.01); *B01L 7/00* (2013.01); *C12M 25/00* (2013.01); *C12M 29/00* (2013.01);
(Continued)

(58) Field of Classification Search
None
See application file for complete search history.

(56) References Cited

U.S. PATENT DOCUMENTS

| 5,255,976 A | 10/1993 | Connelly |
| 5,616,301 A | 4/1997 | Moser et al. |

(Continued)

FOREIGN PATENT DOCUMENTS

| CA | 2 829 515 C | 9/2017 |
| CN | 1284127 A | 2/2001 |

(Continued)

OTHER PUBLICATIONS

De Bruyn et al. "Sandwich-cultured hepatocytes: utility for in vitro exploration of hepatobiliary drug disposition and drug-induced hepatotoxicity." Drug Metabolism & Toxicology, 9:5, 589-616 (Mar. 2, 2013). (Year: 2013).*

(Continued)

*Primary Examiner* — William H. Beisner
(74) *Attorney, Agent, or Firm* — Crowell & Moring LLP

(57) ABSTRACT

Application of the present invention enables quantification of fractions of candidate pharmaceutical compounds (a parent compound and its metabolites), one excreted to the basolateral (Basal/Basolateral)-side via transporters and by diffusion, one excreted to the lumen (Apical)-side, and one remained in the cells. This enables determination of the total amount of the administered candidate pharmaceutical compounds and the distribution ratio of the fractions. The kinetics of the administered candidate pharmaceutical com- (Continued)

pounds can be evaluated, thereby enabling in vitro screening of an enormous number of candidate pharmaceutical compounds for drug candidates exhibiting the efficacy. The object of the present invention is to provide an apparatus and method for understanding a total picture of pharmacokinetics in vitro by quantifying a fraction of basolateral (Basal/Basolateral) efflux, a fraction of lumen (Apical)-side excretion, and a fraction remaining in a cell of a drug which has been administered to the cell to determine the distribution ratio of each fraction.

13 Claims, 12 Drawing Sheets

Related U.S. Application Data continuation of application No. 14/914,278, filed as application No. PCT/JP2014/081135 on Nov. 26, 2014, now Pat. No. 9,880,153.

(51) Int. Cl.

| | | |
|---|---|---|
| G01N 33/15 | (2006.01) | |
| G01N 35/00 | (2006.01) | |
| G01N 35/04 | (2006.01) | |
| B01L 7/00 | (2006.01) | |
| C12M 1/12 | (2006.01) | |
| C12M 1/00 | (2006.01) | |
| C12M 1/34 | (2006.01) | |
| B01L 3/00 | (2006.01) | |
| B01L 9/00 | (2006.01) | |

(52) U.S. Cl.
CPC ............ *C12M 41/46* (2013.01); *C12M 47/20* (2013.01); *G01N 33/15* (2013.01); *G01N 33/502* (2013.01); *G01N 35/1009* (2013.01); *B01L 3/5085* (2013.01); *B01L 9/543* (2013.01); *G01N 2035/00425* (2013.01); *G01N 2035/0418* (2013.01)

(56) References Cited

U.S. PATENT DOCUMENTS

| | | | |
|---|---|---|---|
| 6,277,655 | B1 | 8/2001 | Sarkadi et al. |
| 8,361,785 | B2 | 1/2013 | Oldham et al. |
| 9,880,153 | B2 | 1/2018 | Takahashi et al. |
| 10,684,276 | B2 * | 6/2020 | Takahashi ........... G01N 35/1009 |
| 2001/0019846 | A1 | 9/2001 | Sarkadi et al. |
| 2004/0009572 | A1 | 1/2004 | Felice et al. |
| 2005/0048464 | A1 | 3/2005 | Tian et al. |
| 2007/0184548 | A1 | 8/2007 | Tan et al. |
| 2010/0318032 | A1 | 12/2010 | Togawa |
| 2011/0269232 | A1 | 11/2011 | Takahashi et al. |
| 2012/0183989 | A1 | 7/2012 | Matsui et al. |
| 2013/0164335 | A1 | 6/2013 | Chen et al. |
| 2014/0024070 | A1 | 1/2014 | Izumi et al. |
| 2016/0209403 | A1 | 7/2016 | Takahashi et al. |

FOREIGN PATENT DOCUMENTS

| | | |
|---|---|---|
| CN | 101977643 A | 2/2011 |
| CN | 102272288 A | 12/2011 |
| CN | 103182085 B | 6/2017 |
| EP | 2 293 063 A1 | 3/2011 |
| EP | 2 471 908 A1 | 7/2012 |
| EP | 2 471 908 A4 | 11/2013 |
| JP | 8-503610 A | 4/1996 |
| JP | 2008-503204 A | 2/2008 |
| JP | 2012-65659 A | 4/2012 |
| JP | 2015-105842 A | 6/2015 |
| WO | WO 94/01217 A1 | 1/1994 |
| WO | WO 94/12662 A1 | 6/1994 |
| WO | WO 99/28437 A1 | 6/1999 |
| WO | WO 00/55355 A2 | 9/2000 |
| WO | WO 2005/118787 A2 | 12/2005 |
| WO | WO 2011/024592 A1 | 3/2011 |
| WO | WO 2012/121261 A1 | 9/2012 |

OTHER PUBLICATIONS

Mohamed et al. "In Vitro Investigation of Amyloid-b Hepatobiliary Disposition in Sandwich-Cultured Primary Rat Hepatocytes." Drug Metab Dispos 41:1787-1796, Oct. 2013. (Year: 2013).*
Extended European Search Report issued in counterpart European Application No. 17186423.4 dated Oct. 13, 2017 (11 pages).
Chinese Office Action issued in counterpart Chinese Application No. 201480040060.4 dated Sep. 13, 2016 (9 pages).
Lalloo et al., "Membrane transport of camptothecin: facilitation by human P-glycoprotein (ABCB1) and multidrug resistance protein 2 (ABCC2)", May 4, 2004, 12 pages, vol. 2, No. 1, BMC Medicine, Biomed Central Ltd., XP 021010006.
European Search Report issued in counterpart European Application No. 14866627.4 dated Aug. 22, 2016 (10 pages).
Takahashi et al., "Novel multiple assessment of hepatocellular drug disposition in a single packaged procedure", Dec. 20, 2015, pp. 167-171, vol. 31, No. 2, Drug Metabolism and Pharmacoki netics, XP05529539B.
N. Zelcer et al., "Characterization of Drug Transport by the Human Multidrug Resistance Protein 3 (ABCC3)," The Journal of Biological Chemistry, vol. 276, No. 49 (2001 ), pp. 46400-46407.
International Search Report (PCT/ISA/210) issued in PCT Application No. PCT/JP2014/081135 dated Mar. 3, 2015 with English-language translation (4 pages).
Japanese-language Written Opinion (PCT/ISA/237) issued in PCT Application No. PCT/JP2014/081135 dated Mar. 3, 2015 (5 pages).
Written Opinion of the International Search Authority (Form PCT/ISA/237) dated Mar. 3, 2015 with English-language translation (12 pages).
Kenta Yoshida et al., Calculation of the contribution rate of transporters involved in the biliary excretion of drugs using sandwich-cultured hepatocytes (as translated), Jpn Pharmacol Thr, vol. 37, pp. S53-S58, 2009.
Japanese-language Office Action dated Feb. 5, 2019, and issued in counterpart Japanese Application No. 2018-007821 (four (4) pages).
Chinese-language Office Action issued in counterpart Chinese Application No. 201710862144.1 dated Jul. 18, 2019 (five pages).
Chinese-language Office Action issued in Chinese Application No. 201710860736.X dated May 15, 2020 with English translation (10 pages).
Liu et al., "Biliary Excretion of Taurocholate (TC) in Rat Hepatocytes Cultured in a Collagen Sandwich Configuration (SC)," Hepatology, Jan. 1, 1996, p. 370A, vol. 24, No. 4, Part 02, John Wiley & Sons, Inc., US, XP000861956 (one (1) page).
Extended European Search Report issued in European Application No. 20154632.2 dated Aug. 24, 2020 (13 pages).

* cited by examiner

Fig. 2

|  | Step 0 | Step 1 | Step 2 | Step 3 | Step 4 | Step 5 | Step 6 |
|---|---|---|---|---|---|---|---|
| Plate temperature | 37°C | 37°C | 37°C→4°C | 4°C | 37°C→4°C | (Different depending on sequences) | Room temperature |
| [Sequence 1] 37°C disrupted system | Culture | Washing cells twice with Hanks' solution, and then conditioning with Hanks' solution for 10 minutes. Then, removing Hanks' solution. | Administering drug solution, after 30 minutes, cooling plate to 4°C, and removing drug solution. | Washing three times with ice cold Hanks' solution. | Adding Hanks' solution, after 30 minutes, cooling plate to 4°C, and collecting supernatant. | Adding Hanks' solution containing EGTA and, after 30 minutes, collecting supernatant. | (Fluorescence measurement) Adding 1% Triton X-100 solution and collecting total amount of cell lysate. (LCMS analysis) Adding methanol and collecting total amount of cell lysate. |
| [Sequence 2] 37°C maintained system |  |  |  |  |  | Adding Hanks' solution and, after 30 minutes, collecting supernatant. |  |
| [Sequence 3] 4°C maintained system |  |  |  |  |  | Adding Hanks' solution and, after 30 minutes, collecting supernatant. |  |

Fig. 3

| | Step 4 | Step 5 | Step 6 | Image view |
|---|---|---|---|---|
| [Sequence 1] 37°C disintegrated system | Basolateral efflux I Diffusion(1)' +TP(2)' ⓈⒷ | Biliary excretion(3) + Basolateral efflux II Diffusion(1)+TP(2) Ⓑ1 | Remaining in cell (4) Ⓒ1 | (1), (2)(3) |
| [Sequence 2] 37°C maintained system | Basolateral efflux I Diffusion(1)' +TP(2)' Ⓢ2 | Basolateral efflux II Diffusion(1)+TP(2) Ⓑ2 | Remaining in cell (4) + Biliary excretion (3) Ⓒ2 | (1), (2) |
| [Sequence 3] 4°C maintained system | Basolateral efflux I Diffusion(1)' +TP(2)' Ⓢ3 | Basolateral efflux II Diffusion(1) Ⓑ3 | Remaining in cell (4) + Biliary excretion (3) Ⓒ3 | (1) |

Different wells, but same experiment (S1≒S2≒S3) Actual measurement is required for calculation of relative values Pattern 1  Ⓑ# Ⓒ# = (1)+(2)+(3)+(4) ⇒ 100%

Pattern 2  Ⓢ#+Ⓑ# Ⓒ# =(1)'+(2)'+(1)+(2)+(3)+(4) ⇒ 100%

Fig. 4

| Step | Definition | Pattern 1 | Pattern 2 | Fraction | Corresponding to |
|---|---|---|---|---|---|
| 4 | First fraction of basolateral efflux (1)'+(2)' | | 70.82 | Sup | S1 |
| 5 | Biliary excretion · Second fraction of basolateral efflux (1)+(2)+(3) | | 24.32 | | B1 |
| | Second fraction of basolateral efflux (1)+(2) | | 18.90 | | B2 |
| | Second fraction of basolateral efflux (only by diffusion) (1) | 38.15 | 11.13 | ExEfx-Dif | B3 |
| | Second fraction of basolateral efflux (only by transporter) (2) | 26.60 | 7.76 | ExEfx-TP | B2-B3 |
| | Biliary excretion (3) | 18.58 | 5.42 | BCEfx | B1-B2 |
| 6 | Fraction remaining in cells (4) | 16.67 | 4.86 | Cell | C1 |
| | Biliary excretion · Fraction remaining in cells (3)+(4) | 30.88 | 9.01 | | C2 |
| Total | | 100.00 | 100.00 | | |

Fig. 5
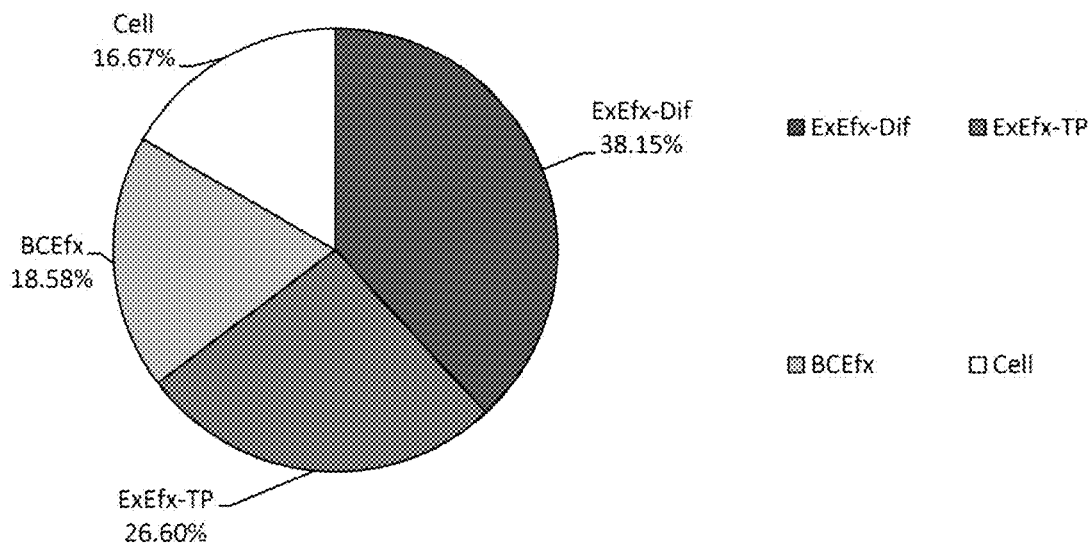
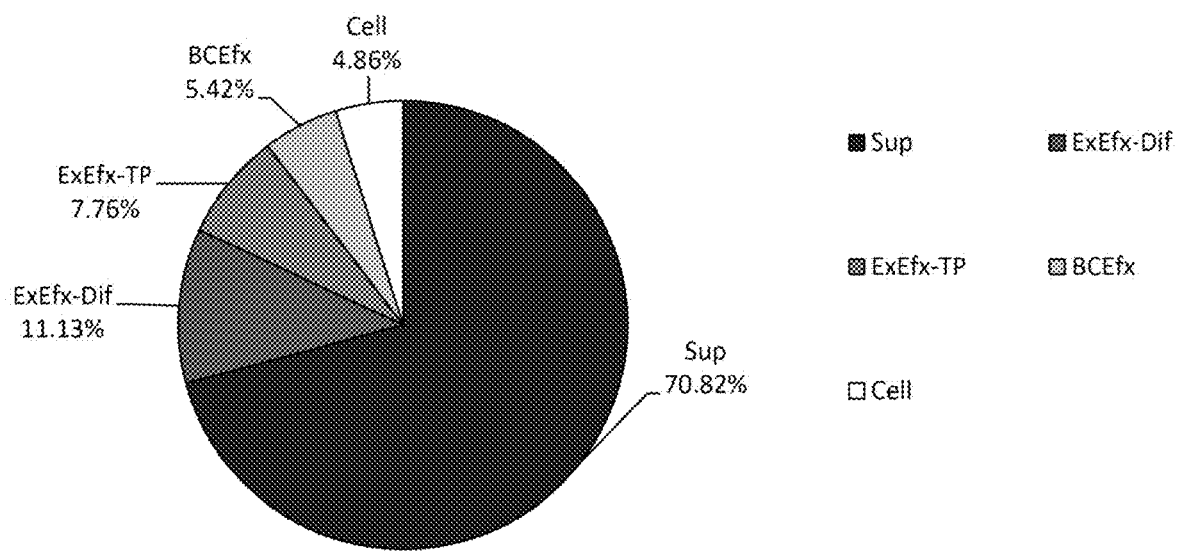

Fig. 6
Circle graph of pattern 1: 10 uM Rhodamine 123
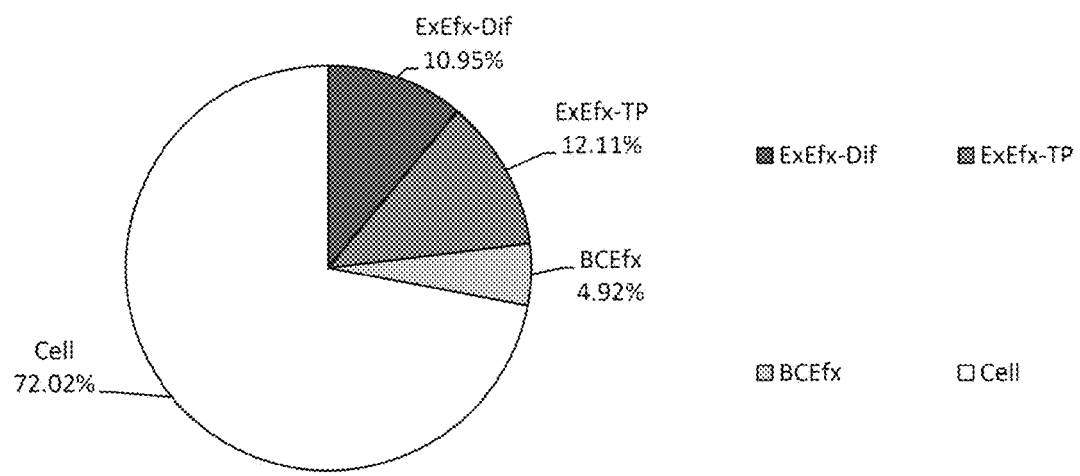
Circle graph of pattern 2: 10 uM Rhodamine 123
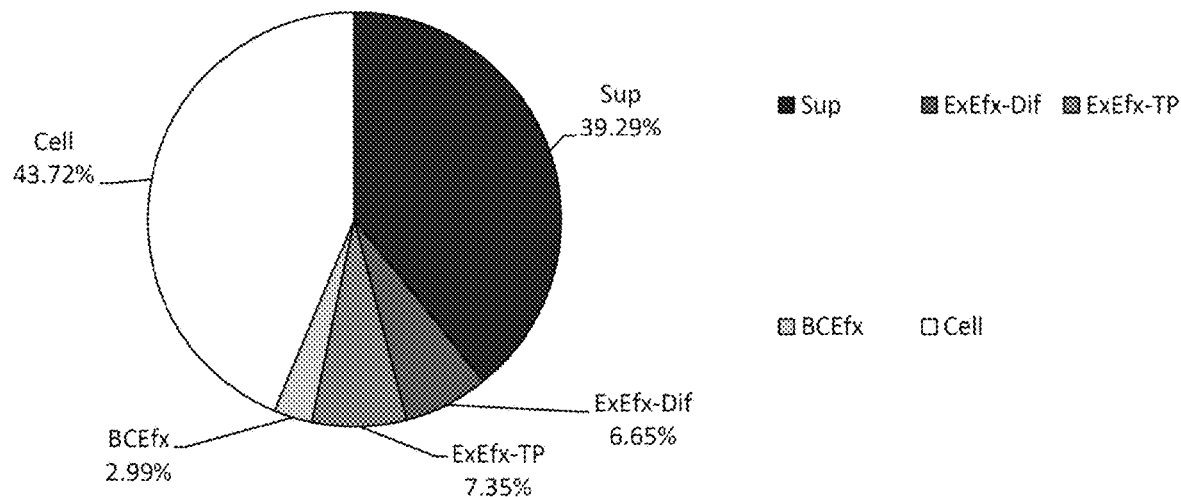

Fig. 10A

| Step number | Substep number | Operation | Plate temperature |
|---|---|---|---|
| 0 | 1 | Culture of cell | 37°C |
| - | 2 | Transferring culture plate containing cell from culture unit to sample preparation unit and setting plate to sample preparation unit | 37°C |
| 1 | 3 | Removing medium from set culture plate | 37°C |
| 1 | 4 | Aspirating buffer from drug solution rack | 37°C |
| 1 | 5 | Adding buffer to wells in culture plate | 37°C |
| 1 | 6 | Removing buffer from wells in culture plate | 37°C |
| 1 | 7 | Repeating 4-6 twice | 37°C |
| 1 | 8 | Aspirating buffer from drug solution rack | 37°C |
| 1 | 9 | Adding buffer to culture plate and conditioning for 10 minutes | 37°C |
| 1 | 10 | Removing buffer from wells in culture plate | 37°C |
| 2 | 11 | Aspirating drug solution from drug solution rack | 37°C |
| 2 | 12 | Adding drug solution to plate and incubating for 30 minutes | 37°C |
| 2 | 13 | Cooling culture plate holder from 37°C to 4°C | 37°C→4°C |
| 2 | 14 | Removing drug solution from wells in culture plate | 4°C |
| 3 | 15 | Aspirating buffer adjusted to 4°C from drug solution rack | 4°C |
| 3 | 16 | Adding buffer to wells in culture plate | 4°C |
| 3 | 17 | Removing buffer from wells in culture plate | 4°C |
| 3 | 18 | Repeating 13-15 three times | 4°C |
| - | 19 | Warming culture plate holder from 4°C to 37°C | 4°C→37°C |
| 4 | 20 | Aspirating buffer from drug solution rack | 37°C |
| 4 | 21 | Adding drug solution to plate and incubating for 30 minutes | 37°C |
| 4 | 22 | Cooling culture plate holder from 37°C to 4°C | 37°C→4°C |
| 4 | 23 | Collecting supernatant from wells in culture plate to another multiple well plate | 4°C |
| - | 24 | Warming culture plate holder from 4°C to 37°C | 4°C→37°C |

Fig. 10B

| Step number | Substep number | Operation | Plate temperature |
|---|---|---|---|
| 5 | 25 | [Wells for sequence 1]<br>Aspirating buffer containing EGTA from drug solution rack | 37°C |
| 5 | 26 | [Wells for sequence 1]<br>Adding buffer containing EGTA to culture plate and incubation for 30 minutes | 37°C |
| 5 | 27 | [Wells for sequence 2]<br>Aspirating buffer from drug solution rack | 37°C |
| 5 | 28 | [Wells for sequence 2]<br>Adding buffer to culture plate and incubation for 30 minutes | 37°C |
| 5 | 29 | [Wells for sequence 3]<br>Aspirating buffer from drug solution rack | 4°C |
| 5 | 30 | [Wells for sequence 3]<br>Adding buffer to culture plate and incubation for 30 minutes | 4°C |
| 5 | 31 | [Wells for sequence 1]<br>Collecting supernatant from wells for sequence 1 to another multiple well plate | 37°C |
| 5 | 32 | [Wells for sequence 2]<br>Collecting supernatant from wells for sequence 2 to another multiple well plate | 37°C |
| 5 | 33 | [Wells for sequence 3]<br>Collecting supernatant from wells for sequence 3 to another multiple well plate | 4°C |
| - | 34 | Changing temperature of culture plate holder from 37°C/4°C to room temperature | 37°C/4°C →Room temperature |
| 6 | 35 | Aspirating 1% Triton X-100 or pure water/methanol from drug solution rack | Room temperature |
| 6 | 36 | Adding 1% Triton X-100 or pure water methanol | Room temperature |
| 6 | 37 | Collecting total amount of cell suspension | Room temperature |
| - | 38 | Transfer plate having collected drug solution to measurement unit | - |
| - | 39 | Measurement with plate reader or LCMS | - |
| - | 40 | Calculation of distribution ratio and score of respective fractions from measurement result | - |
| - | 41 | Displaying calculated values on display unit | - |

COMPONENTIAL ANALYZER, DRUG EFFICACY ANALYZER, AND ANALYSIS METHOD

CROSS REFERENCE TO RELATED APPLICATIONS

This application is a continuation of U.S. application Ser. No. 15/847,092, filed Dec. 19, 2017 which is a continuation of U.S. application Ser. No. 14/914,278, filed Feb. 25, 2016, now U.S. Pat. No. 9,880,153, issued Jan. 30, 2018, which is a National Stage of International Patent Application No. PCT/JP2014/081135, filed Nov. 26, 2014, which claims the benefit of JP 2013-246906, filed Nov. 29, 2013, the entire disclosures of which are herein expressly incorporated by reference.

TECHNICAL FIELD

The present invention relates to an in vitro evaluation of a total picture of pharmacokinetics, including uptake, metabolism, and excretion, useful for new drug development.

BACKGROUND ART

The process of new drug development necessarily involves conducting a clinical trial ("human clinical trial"), which involves administration into the human body and verification of the effect, under the regulation of the Act on Pharmaceuticals and Medical Devices and such human clinical trials and animal testing entail enormous development costs. The cost of overall new drug development has recently increased with these development costs being the greatest cause. A major cause of the cost is that insufficient efficacy and toxicity of some drug candidates are not detected in non-clinical animal experiments in the earlier period of the development process and the insufficient efficacy or the toxicity may be found for the first time in a human clinical trial in the later period of the development process, failing to avoid useless development costs and costs for the human clinical trial.

In this context, it is important to select new drug candidate that have the efficacy and no toxicity early in order to increase the clinical success rate and reduce the new drug development cost. Therefore, many pharmaceutical companies desire in vitro evaluation systems allowing good predictions of pharmacokinetics of administered drugs in the human body using human cells in an early stage of drug development, instead of narrowing down drug candidates solely depending on animal experiments, which have poor correlations with properties of human cells. However, no techniques have been established to attain and analyze total pictures of pharmacokinetics, including uptake, metabolism, excretion through bile ducts and blood vessels, of administered candidate pharmaceutical compounds using cells.

A drug needs to be taken up by the liver and metabolized there into a metabolite or left as an original compound (a parent compound) without being metabolized, then excreted to the basolateral side, and recirculated in the bloodstream to the target organ in order to exhibit its efficacy in the body. Therefore, such an in vitro testing system that can measure the amount of a recirculating candidate pharmaceutical compound excreted to the basolateral side after administration and evaluate the efficacy, which is one of the most important indexes in the new drug development, could be a very useful pharmacokinetics evaluating system. In addition, such a testing system would provide a total picture of the pharmacokinetics including the amount excreted from cells into bile duct (the amount of loss), which is the amount excreted into a bile duct and then out of the body as urine or feces, and the amount retained in the cells and thereby the distribution ratio of such fractions.

Patent Literature 1 and 2 disclose techniques for administering a drug to culture cells and evaluating the amount excreted from bile ducts of the cells (the amount of loss). These evaluation methods evaluate the amount of drug loss, which is an amount of a drug that is administered, but excreted into a bile duct without exhibiting toxicity or efficacy and then excreted out of the body as urine or feces.

CITATION LIST

Patent Literature

Patent Literature 1: JP Patent Publication No. 2012-65659 A
Patent Literature 2: JP Patent Publication No. 8-503610 A (1996)

SUMMARY OF INVENTION

Technical Problem

The methods of the conventional art are methods for evaluating the amount of biliary excretion, which is an amount of a component having no efficacy, that is, a method for evaluating an amount lost from the body. In order to obtain information on a component having efficacy, it is desired to evaluate directly the amount of the component excreted to the basolateral side. In the conventional art, however, a method for analyzing the amount of a component excreted into the basolateral side was not established. Furthermore, unlike the systems that can evaluate only a part of pharmacokinetics, a system that quantifies the administered drug in fractions, as to where in the cells the administered drug is excreted and where is the drug is retained, such as one excreted to the basolateral side (the basal/basolateral side), one excreted into the lumen side (the apical side), and one retained in the cells, provides a total picture of pharmacokinetics in vitro, thereby enabling a highly accurate evaluation of the efficacy. However, such an evaluation method has not been established in the conventional art either.

Solution to Problem

For example, provided is a componential analyzer comprising: a temperature controlling unit for controlling temperature in a plurality of containers; and an analyzing unit for measuring a component in the plurality of containers and analyzing the measured component; wherein the plurality of containers includes at least a first container and a second container; the first container and the second container each contain a first buffer solution; the temperature controlling unit controls temperature in the first container and temperature in the second container so that the temperatures are different from each other; and the analyzing unit measures an amount of the component excreted from a cell in the first container to the first buffer solution in the first container and an amount of the component excreted from a cell in the second container to the first buffer solution in the first container, and analyzes an amount of the component excreted via transporters in the cells.

Effects of Invention

Application of the present invention enables direct evaluation of components, such as drugs, excreted to the basolateral side of cells. Furthermore, quantification of fractions of candidate pharmaceutical compounds (a parent compound and its metabolites), one excreted to the basolateral (basal/basolateral) side by transporters and/or diffusion, one excreted to the lumen (apical) side, and one remained in the cells, and determination of the total amount of the administered candidate pharmaceutical compounds and the distribution ratio of the fractions enable evaluation of the kinetics of the administered candidate pharmaceutical compounds, thereby improving the accuracy of in vitro screening of an enormous number of candidate pharmaceutical compounds for drug candidates exhibiting the efficacy. As a result, it becomes possible to select candidate pharmaceutical compounds in an early stage and reduce useless animal experiments and unnecessary human clinical trials. It contributes to the reduction of attrition rate, which are heavy loads for pharmaceutical companies.

BRIEF DESCRIPTION OF DRAWINGS

FIG. 2 illustrates a flow of sample preparation.
FIG. 3 illustrates fractions quantified in steps 4, 5, and 6 and image view of drug distribution.
FIG. 4 illustrates definitions of fractions and results of CDF.
FIG. 5 illustrates the distribution ratio of CDF.
FIG. 6 illustrates the distribution ratio of Rhodamine 123.
FIG. 10A is a flow chart of operations of the automatic measuring apparatus.
FIG. 10B is a flow chart of operations of the automatic measuring apparatus.

DESCRIPTION OF EMBODIMENTS

Embodiment 1

In this embodiment, the aforementioned method of componential analysis for evaluation of efficacy is described in connection with steps 0-6 in FIG. 2. Steps 4-6 are described in detail referring to FIG. 3.

In the following plural embodiments, the present invention is described in connection with methods for evaluating medicinal properties. However, these are examples for illustrating the claimed invention and the methods of componential analysis according to the claimed invention can be, needless to say, used to evaluate chemical substances other than drug and also to evaluate drug metabolites. Moreover, specific conditions such as buffer solution, temperature, and time indicated in these embodiments are for the illustration purpose and other conditions having similar effects without departing from the technical idea of the present invention can be, needless to say, used.

This embodiment describes a method using at least 3 sequences including sequences 1-3. Each sequence contains a holding region for holding cells. These holding regions may contain separate containers for respective sequences or one container may be divided into a plurality of holding regions for respective sequences.

<Step 0: Preparation and Culture of Hepatocytes>

In this step, preparation and culture of hepatocytes are conducted to examine the effect of the drug. An example is illustrated below.

Hepatocytes were prepared by in situ collagenase perfusion method. The details are as follows. A rat (5-6 week-old) is anesthetized with pentobarbital and laparotomy is performed to insert a catheter into the portal vein and inject the preperfusion solution (a $Ca^{2+}$ and $Mg^{2+}$ free Hanks' solution containing EGTA). After confirming that blood is sufficiently removed from the liver, the perfusion is stopped. The perfusate is changed into a collagenase solution to conduct perfusion. In this embodiment, the perfusion is conducted with a Hanks' solution containing 0.05% collagenase, but the collagenase solution is not limited to this. Once confirmed that the tissue between the cells was digested by collagenase, the perfusion is stopped. The liver is excised, sliced in a cooled Hanks' solution, and separated into cells by pipetting. Damaged hepatocytes are removed by centrifugation at 500 G for 5 minutes with an isotonic Percoll solution. The viability of the resultant hepatocytes is determined by the trypan blue-exclusion test. Hepatocytes having a viability of 85% or more are used for culture. Here, hepatocytes having a viability of 85% or more are used for culture, but such culture is, needless to say, not necessarily limited to the condition. In addition, the preparation of hepatocytes is not necessarily limited to that by in situ collagenase perfusion method. The hepatocytes to be used are not limited to those derived from a rat and the strain of rat is not limited. This embodiment uses hepatocytes, but cells are not limited to this.

Figure 1:
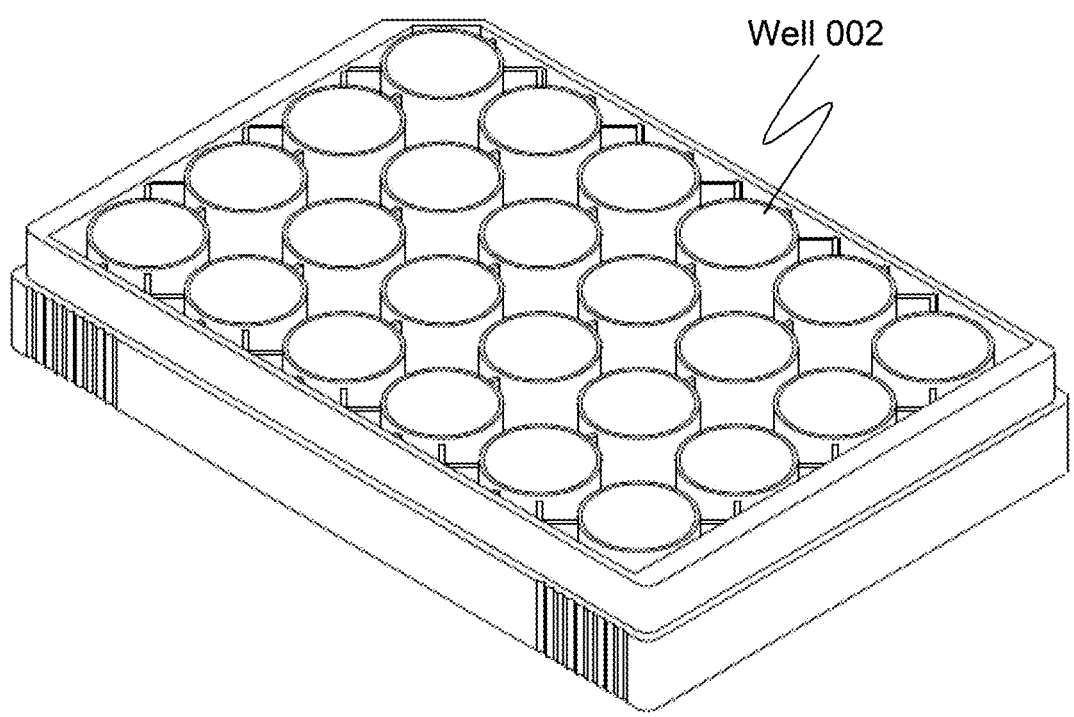
FIG. 1 illustrates a culture plate.

Hepatocytes prepared by in situ collagenase perfusion method as described above are suspended in a medium. The hepatocytes are suspended at a density of $5\times10^5$ cells/mL in a medium and plated onto a commercially available culture dish coated with collagen. The density upon plating, the medium, and the culture plate 001 are not particularly limited. The culture plate is illustrated in FIG. 1. A 24 well culture plate having 24 culture regions (wells, 002) is here illustrated, but the culture plate is not limited to this as long as it can contain predetermined cells and containers in other shapes may be used. After plating, culture is started under conditions of 5% $CO_2$ and 37° C. using a $CO_2$ incubator. After 18 hours or more, the first medium change is conducted. Although the medium to be used for culture 18 hours after the plating is not particularly limited, in this embodiment, the medium (FCS−), a medium in which FCS is removed from the medium (10% FCS+), supplemented with Matrigel is used. After this, medium change with the medium (FCS−) is conducted every 24 hours. As described later, testing is conducted under three different conditions (sequences 1, 2, and 3: described in detail in step 5) in step 5, three independent culture plates with the same conditions are prepared at this point. In steps 0 to 4 and step 5, the same testing operations are conducted in all the three sequences.

<Step 1: Conditioning of Hepatocytes>

In this step, the cells cultured in step 0 are conditioned in a suitable condition for the drug evaluation. An example is illustrated below.

The culture supernatant of the cells cultured in step 0 for 4 days is removed and 400 μL of Hanks' solution is added as a buffer. The cells are incubated at 37° C. for 10 minutes (FIG. 2, step 1). The type and amount of buffer are not particularly limited.

Preferably, the operations of step 1 are repeated twice. By replacing the medium used in the culture of step 0 with buffer solution (e.g., Hanks' solution) and adapting the cells to the buffer ingredients, they are conditioned for the accurate measurement and analysis in the following steps. The number of times step 1 is repeated can be, needless to say, changed depending on the types of buffer solution and cells used.

<Step 2: Administration of Drug Solution>

In this step, the drug solution to be evaluated is administered to cells. An example is illustrated below.

The buffer is removed, and then 200 μL of 10 μM CDF (a fluorescent reagent) is added to the well. The plate is incubated at 37° C. for 30 minutes and then maintained at 4° C. for 5 minutes (FIG. 2, step 2). The type, concentration, and amount of the reagent are not particularly limited. CDF emits fluorescence and can be therefore easily quantified by a plate reader as a model reagent. The amount of administration, 200 μL, was chosen so that the cells as a whole in the well would be immersed in the reagent. The concentration of CDF may be a concentration conventionally used for a fluorescence assay of cells. This concentration is preferably applied as an amount of the reagent for the detection with a plate reader. 30 minutes of the incubation time was determined based on the result of a preliminary examination that the time required for getting the equilibrium between uptake and excretion of a drug is 30 minutes. The plate temperature was lowered to 4° C. after incubation for 30 minutes for the purpose of preventing the leakage of the administered drug from the cells. This is because lowering the temperature in the container prevents cells from excreting the drug.

As a result of thus lowering the temperature of drug to a predetermined temperature or lower, the drug remains in the cells and the leakage of the drug from the cells can be suppressed. In this embodiment, the temperature is lowered to 4° C., but the temperature may be any temperature as long as the leakage of the administered drug from the cells can be suppressed at the temperature. The method for the suppression is not limited to lowering the temperature, but can be any method by which leakage of the administered drug from the cells can be suppressed, for example, by administering an inhibitor. In any case, the temperature in step 2 is lower than the plate temperature in step 1. This is because the temperature for the conditioning in step 1 is preferably a temperature that activates absorption and excretion of the drug by cells (e.g., 37° C.), in contrast to step 2.

The timing of the drug administration is not limited to that of this embodiment. For example, the drug may be administered on the day before or a few days before the testing day. In this case, the drug may be administered in step 0 and steps 1 and 2 can be omitted.

<Step 3: Washing of Cells>

In this step, the drug solution other than that transferred into the cells in step 3 is washed away. An example is described below.

The cells were then washed 3 times with 400 μL, of ice-cold Hanks' solution while keeping the plate at 4° C. (FIG. 2, step 3). The purpose of keeping the plate at 4° C. is the same as that described above. The amount of the Hanks' solution for washing was determined to be 400 μL, for the purpose of removing medium ingredients remaining on the inner wall of the well because the amount of the medium in culture is 400 μL. The number of washing in general biochemistry assays is usually three times, which is adopted here. Conditions for the washing are not limited. This step removes anything other than the drug solution to be measured, making it possible to improve the accuracy of the efficacy evaluation in the later steps.

<Step 4: Collection of Fraction of Basolateral Efflux>

As an index for evaluating efficacy, it is effective to analyze whether the administered drug tends to remain in the cell for a long time or only for a short time. Therefore, this step aims to obtain the data for the aforementioned index and the drug is leaked from the cells in a predetermined time before evaluating the cells in respective sequences in step 5 described later. An example is illustrated below.

A buffer solution (e.g., Hanks' solution) for the pretreatment is first administered, the plate is incubated at 37° C. for 30 minutes, and the Hanks' solution (supernatant) containing the drug was collected (FIG. 2, step 4). The buffer solution may be the same as or different from the buffer solution used in step 5. The plate was maintained at 37° C. so that the drug accumulated in the hepatocytes (FIG. 3, 101) by step 3 is excreted into the Hanks' solution via the first basolateral efflux, that is, the passively diffusion (FIG. 2, step 4, (1)') and/or via the transporter (TP) (FIG. 2, step 4, (2)' and 102 in the image view). Because basolateral efflux occurs also in step 5 as described later, for the distinguishment, the basolateral efflux in step 4 is defined as the first basolateral efflux and the basolateral efflux in step 5 as the second basolateral efflux. Essentially, both steps represent the basolateral efflux(supernatant). Transporters are membrane proteins that are responsible for transportation of substance and expressed on the cell membrane. They are responsible for active transportation of substance between inside and outside of the cell. The passive diffusion is excretion to outside of the cell other than that via the transporter and includes the leakage through the cell membrane. The drug excreted into the Hanks' solution in step 4 was defined as a fraction of basolateral efflux, because the upper surface of the cells facing the Hanks' solution corresponds to the basal/basolateral face (FIG. 3, 104), which is considered to be a part facing the blood vessel in the body.

Step 5, which is explained next, includes collecting the drug in three different operations (sequences 1, 2, and 3) and an index for examining whether the drug tends to remain in the cell can be acquired by, prior to step 5, obtaining the first fraction of basolateral efflux (the drug excreted into Hanks' solution) in step 4 as mentioned above.

The Hanks' solution used to obtain the fraction of the basolateral efflux may be of any sequence. For example, Hanks' solutions of all sequences 1-3 described later or a part thereof may be evaluated.

Steps 3 and 4 are steps of conducting the analysis according to the present invention in more detail to conduct highly accurate evaluation. The present invention can be carried out skipping steps 3 and 4 and conducting operations of step 5. The aforementioned steps 0-4 are conducted in at least sequences 1-3, as shown in FIG. 2. In step 5, operations are conducted under different conditions for sequences 1-3 so as to obtain a plurality of index data sought in the present invention by the analysis described later. An example is illustrated below.

<Step 5, Sequence 1: Collection of Supernatant in 37° C. Disrupted System>

In sequence 1, as shown in sequence 1 in FIG. 3, the drug is excreted from the cell into a buffer solution (e.g., Hanks' (-) solution) in an amount equal to the sum of biliary excretion (3) and the second basolateral efflux (that is, diffusion (1) and excretion via transporter (TP) (2)) discharge. Hanks' (-) solution is Hanks' solution free of calcium and magnesium ions and used, for example, when cell-cell adhesion is not enhanced intentionally as in this sequence. For the purpose of positively removing cell-cell adhesion, a chelator such as EGTA is used as described in the following. Next, 200 µL of Hanks' (-) solution containing 1 mM EGTA was added. EGTA has a chelating effect of suppressing the effect of $Ca^{2+}$ and $Mg^{2+}$ involved in the adhesion of intercellular adhesion molecules and is a reagent for removing cell-cell adhesion. This causes the disruption of bile ducts formed during the culture process. The area was incubated at 37° C. for 30 minutes, and then the supernatant was collected. The chelating reagent is not limited to EGTA, as long as it has a chelating effect. Type and amount of the buffer containing EGTA and temperature and time of the incubation are not particularly limited. In sequence 1 of step 5, the drug remaining in the cells (FIG. 3, step 5 and the image drawing, (1) and (2)) and the drug excreted into the bile canaliculi (FIG. 3, step 5 and the image drawing, (3)) upon the completion of step 4 are all excreted into the supernatant and collected (FIG. 3, step 5, sequence 1). In step 5, (3) is defined as a biliary-excreted fraction, because the cell membrane part around the gap formed in the cell-cell adhesion part corresponds to an apical face (FIG. 3, 105) and the gap is assumed to be a bile canaliculus (FIG. 3, 103). In step 5, sequence 1, the temperature is maintained at 37° C., and therefore the fractions excreted from the cells to the basolateral side include the fraction via passive diffusion (FIG. 3, step 5, (1)) and the fraction via the transporter (FIG. 3, step 5, (2)).

<Step 5, Sequence 2: Collection of Supernatant in 37° C. Maintained System>

In sequence 2, bile ducts are not disrupted as in sequence 1 and the drug is excreted only by the second basolateral efflux (diffusion (1) and transporter (2)) indicated in FIG. 3.

200 µL of Hanks' solution was added. In sequence 2, any chelating agent such as EGTA is not included as in sequence 1, and therefore cell-cell adhesion is maintained. Accordingly, sequence 2 is a sequence where the disruption of bile canaliculi is not induced. The area was incubated at 37° C. for 30 minutes, and then the supernatant was collected. In sequence 2 in step 5, the drug remaining in the cells (FIG. 3, step 5 and the image view, (1) and (2)) upon the completion of step 4 is excreted into the supernatant and collected (FIG. 3, step 5, sequence 2). Following the foregoing description, the drug excreted into the supernatant is defined as a second fraction of basolateral efflux. In step 5, sequence 2, the temperature is maintained at 37° C., and therefore the fractions excreted from the cells to the basolateral side include the fraction via passive diffusion (FIG. 3, step 5, (1)) and the fraction via the transporter (FIG. 3, step 5, (2)).

By quantitatively analyzing the amounts of the drug collected from sequence 1 and sequence 2 in step 5, for example, by subtracting the quantified value of the amount of the drug collected in sequence 2 from the quantified value of the amount of the drug collected in sequence 1, each of the amount of the drug excreted to the bile canaliculi, (3) and the amount of the drug of the second fraction of basolateral efflux can be calculated.

<Step 5, Sequence 3: Collection of Supernatant in 4° C. Maintained System>

Sequence 3 has a temperature condition lower than that in sequences 1 and 2 as described later, and thereby the excretion of the drug via the transporter (1) is suppressed and only the amount of the drug excreted by diffusion (2) is excreted in the second fraction of basolateral efflux.

200 µL of Hanks' solution was added. The area was incubated at 4° C. for 30 minutes, and then the supernatant was collected. The testing temperature is different from step 5 sequence 2, which is also a maintained system. This aims to suppress basolateral efflux via the transporter by cooling to 4° C. In step 5, sequence 3, a sequence having a low temperature of 4° C. is adopted to suppress the transporter activity, and thereby quantify only the amount excreted by passive diffusion (FIG. 3, step 5, (1)). Comparing this with step 5, sequence 2 makes it possible to calculate (quantify) the amount of the basolateral efflux fraction via transporter. For each drug, a specific transporter is present for moving between inside and outside of the cell. Therefore, the ability to exclude the amount of excretion by passive diffusion and quantify the amount of excretion via the transporter means the ability to quantify the amount of excretion specific for the drug. Type and amount of the buffer and temperature and time of the incubation are not particularly limited. As described above, the fraction excreted via the transporter can be calculated by quantifying the drug collected from sequence 2 and sequence 3 in step 5. Although the calculation of excreted fractions using sequences 1, 2, and 3 is illustrated in this embodiment, the number of sequences is not limited to three. For example, when only the separation of biliary excretion (3) and the second basolateral efflux ((1)+(2)) is desired, it is sufficient to conduct only sequences 1 and 2; and when only the separation of the diffusion (1) and the transporter (2) in the second basolateral efflux is desired, it is sufficient to conduct only sequences 2 and 3. It is also possible to measure only the amount excreted by diffusion by additionally having a disrupted system at 4° C., as needed, to suppress biliary excretion in excretion via transporter. For example, comparison of this 4° C. disrupted system with sequence 3 makes it possible to separately evaluate the biliary excretion by diffusion and the biliary excretion via transporter.

The steps in each of sequences 1-3 may be conducted in any order and steps may be conducted in parallel.

<Step 6: Collection of Biliary Fraction and Intracellular Fraction>

In step 6, the same operations are conducted for the 3 sequences again. In step 6, the drug collection for quantifying the fraction remaining in the cells is conducted. When fluorescent agent is quantified using a plate reader, it is preferred that, for example, 200 µL of a Hanks solution containing 1% surfactants is added and suspended and the total amount is collected (FIG. 2, step 6). This disrupts the cell membrane and makes it possible to have the drug remaining in the cells excreted. The resultant samples are transferred to a culture plate and fluorescence was measured using a plate reader. Wells containing only the Hanks' solution are prepared for the blank measurement. Fluorescence intensity is measured with an excitation wavelength of 484 nm and an absorption wavelength of 519 nm.

When the drug is quantified using a mass spectrometry (LCMS) apparatus, water is added for lowering the tonicity, the fraction remaining in the cells are extracted by a treatment with an organic solvent and then suspended with an organic solvent such as methanol, and the total amount is collected (FIG. 2, step 6). Quantification of the drug is subsequently conducted using an LCMS apparatus as described later.

<Determination of Distribution Ratio and Scoring of Respective Fractions Based on Result of Measurement>

The distribution ratio to respective fractions is calculated based on the fluorescence intensities reflecting the amounts of the drug obtained in the aforementioned steps. Here, the sum of steps 5 and 6 (FIG. 3, B #+C #=(1)+(2)+(3)+(4)) is defined as 100% amount of the drug. This is referred to as "pattern 1."

From the six values (B1, B2, B3, C1, C2, C3) obtained by the measurement of fluorescent amount, the distribution ratio of fractions illustrated in pattern 1 in FIG. 4 is obtained. As for these values, the second fraction of the basolateral efflux only by diffusion (Extracellular Efflux by Diffusion, ExEfx-Dif) is expressed as B3;

the second fraction of the basolateral efflux only by the transporter (Extracellular Efflux by Transporter, ExEfx-TP) is expressed as B2-B3;

the fraction of the biliary excretion (Bile Canaliculi Efflux, BCEfx) is expressed as B1-B2; and the fraction remaining in the cells (Cell) is expressed as C1.

Based on this result, a circle graph such as pattern 1 in FIG. 5 can be generated and visual understanding of a total picture of the distribution ratio of respective fractions becomes possible.

Furthermore, scoring of particular drugs as the following becomes possible based on the quantification result. In this embodiment, the scoring calculated for CDF is illustrated. The calculated scores are not limited to these.

A score for evaluating basolateral efflux via transporter is calculated as ratio of the amount of the drug excreted via transporter to the amount of the drug of the second fraction of basolateral efflux (Ratio of Extracellular Efflux by Diffusion, RexEMTP), (B2−B3)/B2.

A score for evaluating the biliary excretion can be calculated as ratio of the amount of the drug excreted into the bile canaliculi to the total amount of the drug taken up into the cells (Biliary Retention Drug, BiRD), (B1−B2)/(C1+C2), or alternatively, ratio of the amount of the drug excreted into bile canaliculi to the amount of the drug remaining in the cells, (C2−C1)/C2 or (B1−B2)/C1, or the like.

<Comparison of Distribution Ratios and Scores Between Different Drugs>

The operations same as those described above can be conducted using Rhodamine123 instead of CDF to obtain the result shown in FIG. 6 (pattern 1). The result indicates that a distribution ratio apparently different from the result of CDF shown in FIG. 5 (pattern 1) can be detected.

For example, the ratio of the amount of drug excreted via transporter to the amount of drug excreted to the basolateral side (RexEMTP) and the ratio of the amount of drug excreted into the bile duct to the total amount of drug taken up into the cells (BiRD) for CDF are 41.08 and 18.58, respectively, while those for Rhodamine123 are 52.52 and 4.92, respectively, indicating that CDF is a drug that has an stronger tendency to be excreted into the bile canaliculi but not to the basolateral side than Rhodamine123 does. As described above, the present invention makes it possible to evaluate compounds on the pharmacokinetics they exhibit.

Embodiment 2

Embodiment 2 describes the determination of distribution ratio and scoring of respective fractions based on the measurement result when a method different from embodiment 1 is used.

In this embodiment, a quantified value S # (corresponding to step 4) described in FIG. 3, in addition to the distribution ratio of respective fractions shown in pattern 1 in embodiment 1, is used to obtain information on whether the administered drug has a strong or weak tendency to remain in the cells, which makes more accurate evaluation possible. Accordingly, the sum of steps 4, 5, and 6 (FIG. 3, S #+B #+C #=(1)'+(2)'+(1)+(2)+(3)+(4)) is defined as the 100% amount of the administration drug. This is referred to as "pattern 2". Accordingly, nine values (S1, S2, S3, B1, B2, B3, C1, C2, C3) obtained in the sequences in steps 4, 5, and 6 can be used as evaluation indexes.

From nine values obtained from measurement of fluorescent amounts, the distribution ratio of respective fractions shown in pattern 2 in FIG. 4 is obtained. As for these values, the first fraction of the basolateral efflux (Sup fraction) is expressed as S1 (≈S2≈S3);

the second fraction of the basolateral efflux only by diffusion (Extracellular Efflux by Diffusion, ExEfx-Dif) is expressed as B3;

the second fraction of the basolateral efflux only by the transporter (Extracellular Efflux by Transporter, ExEfx-TP) is expressed as B2-B3;

the fraction of the biliary excretion (Bile Canaliculi Efflux, BCEfx) is expressed as B1-B2; and the fraction remaining in the cells (Cell) is expressed as C1.

Based on this result, a circle graph such as pattern 2 in FIG. 5 can be generated and visual understanding of a total picture of the distribution ratio of respective fractions becomes possible. As determined by a method described in embodiment 2, the Sup fraction, which is an index for tendency to remain or not to remain in the cells, for CDF is 70.82, while that for Rhodamine123 is 39.29 (FIG. 6, pattern 2), indicating that CDF has a tendency to be excreted to the basolateral side. This is consistent with the evaluation of the fraction remaining in the cells in embodiment 1.

Furthermore, scoring of characteristics of drugs becomes possible based on the quantification result, as described in embodiment 1.

Embodiment 3

Embodiment 3 describes an example of apparatus automating a series of steps described in embodiments 1 and 2. About purposes of operations and functions of configurations of the apparatus described later, descriptions may be omitted when the descriptions are overlapped with those of the aforementioned embodiments 1 and 2.

In the configurations of the apparatus described later, the regions holding cells referred to as sequences 1-3 shown in embodiments 1-2 are described using expressions such as "a well for sequence 1," "a well for sequence 2," and "a well for sequence 3." For example, a plurality of containers in the aforementioned "well culture plate" may be defined for respective sequences or a plurality of wells in a well culture plate may be divided and the divided regions may be defined as, for example, "a first container," "a second container," and "a third container."

As for the well for sequence 1 and the well for sequence 2 in particular, effective evaluation may be provided in terms of accuracy and speed by defining them as wells in divisions of one well culture plate because they are subjected to a substantially the same temperature control.

As for the operations of the apparatus described later, exchange of wells (containers) for respective sequences may be automatic or manual. Descriptions on exchange and placement of the containers will be omitted in the following description.

The apparatus includes a culture unit 106, a sample preparation unit 107 (including an input unit 107A), an analyzing unit 108 and a display unit 109, as shown in FIG.

7. The sample preparation unit 107 has a temperature controlling unit 107B for controlling temperature in respective containers (plates) described later, a liquid-feeding unit 107C capable of supplying or collecting liquid in a container, and the like. The analyzing unit 108 has a measurement unit 108A for measuring the amount of a component such as a drug and analysis unit 108B for analyzing each of: an amount excreted via transporter, an amount excreted via the bile duct, an amount remaining in the cells, and an amount excreted via a route (diffusion) other than the transporter and the bile duct based on the amount of the component such as a drug obtained in the measurement unit. The above conformation of the apparatus is an example and, for example, other configurations may be, needless to say, adopted, for example, one in which only the analysis unit operates in a separate apparatus and the information obtained by the measurement unit is transmitted to the separate apparatus.

Figure 8:
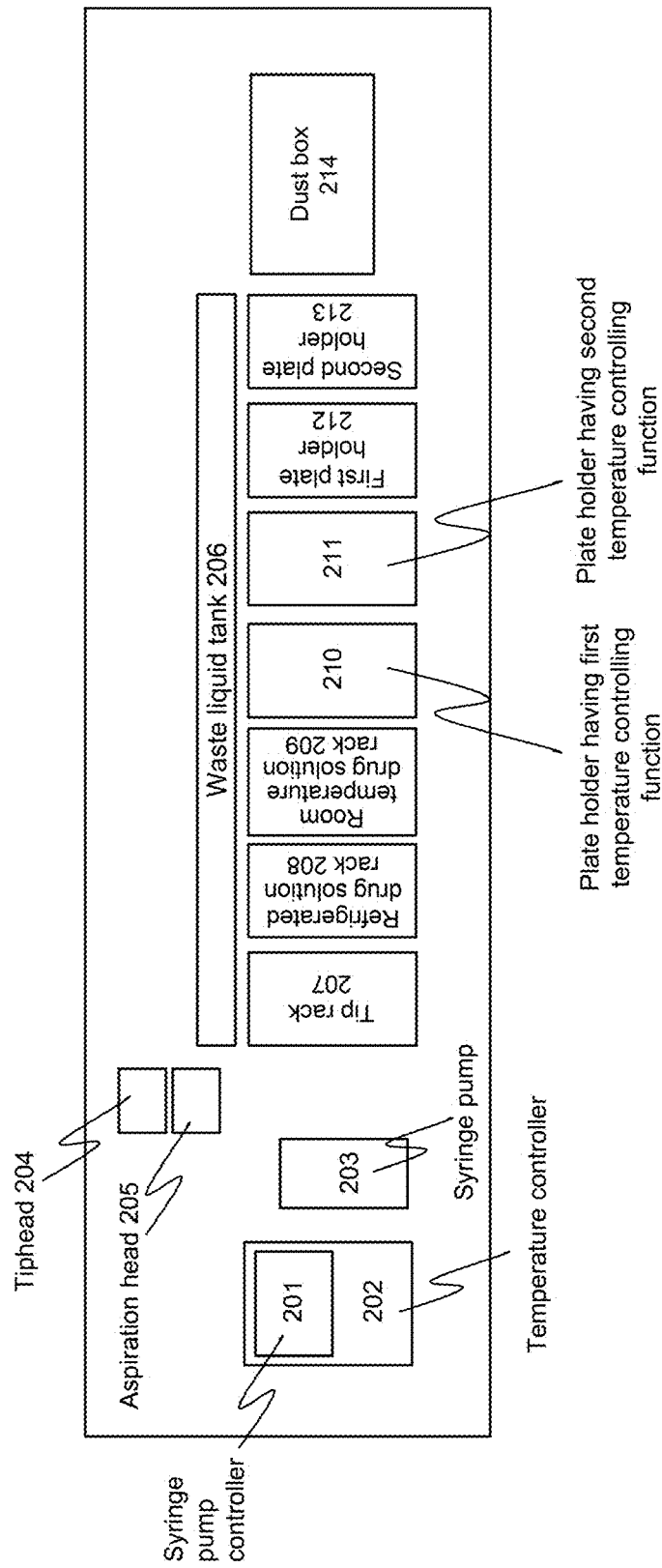
FIG. 8 is a top view of a sample preparation unit.
Figure 9:
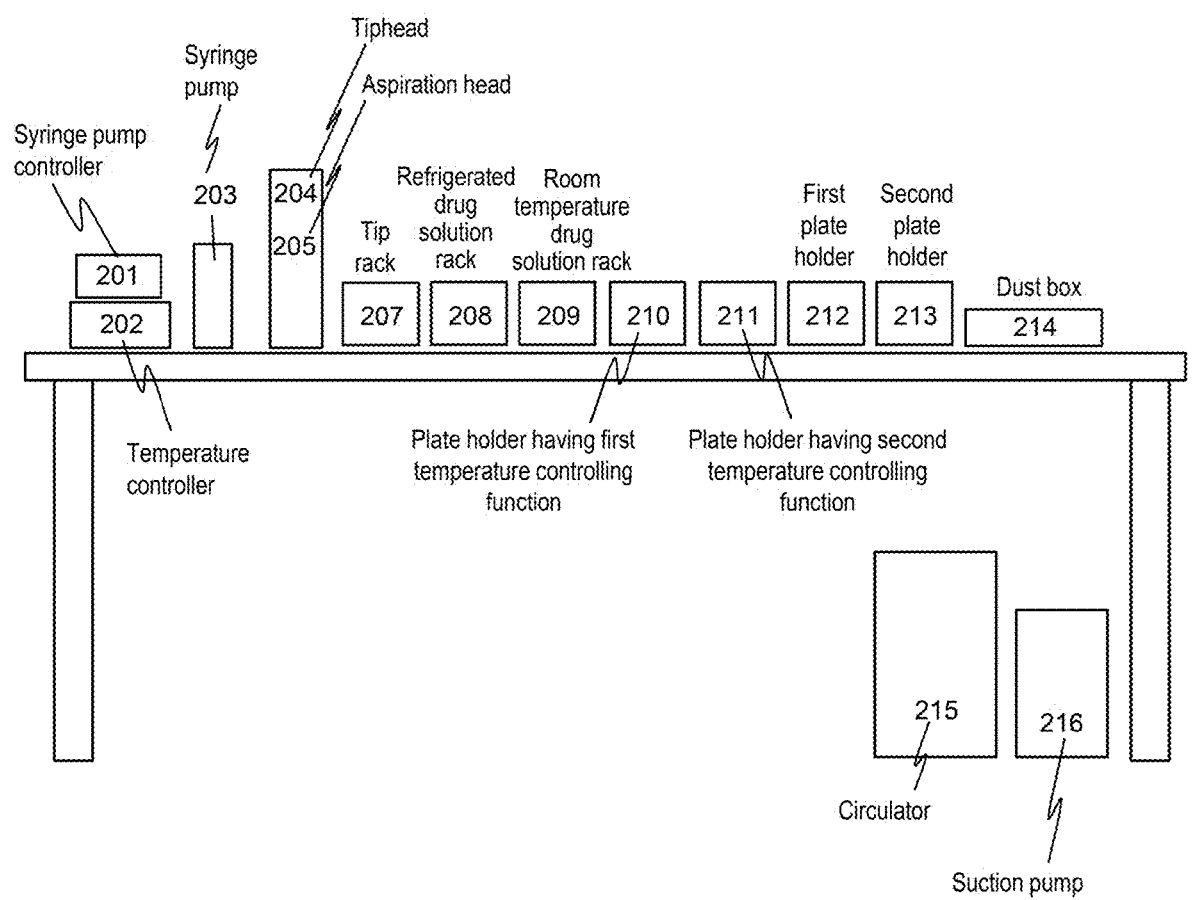
FIG. 9 is a front view of the sample preparation unit.
Figure 11:
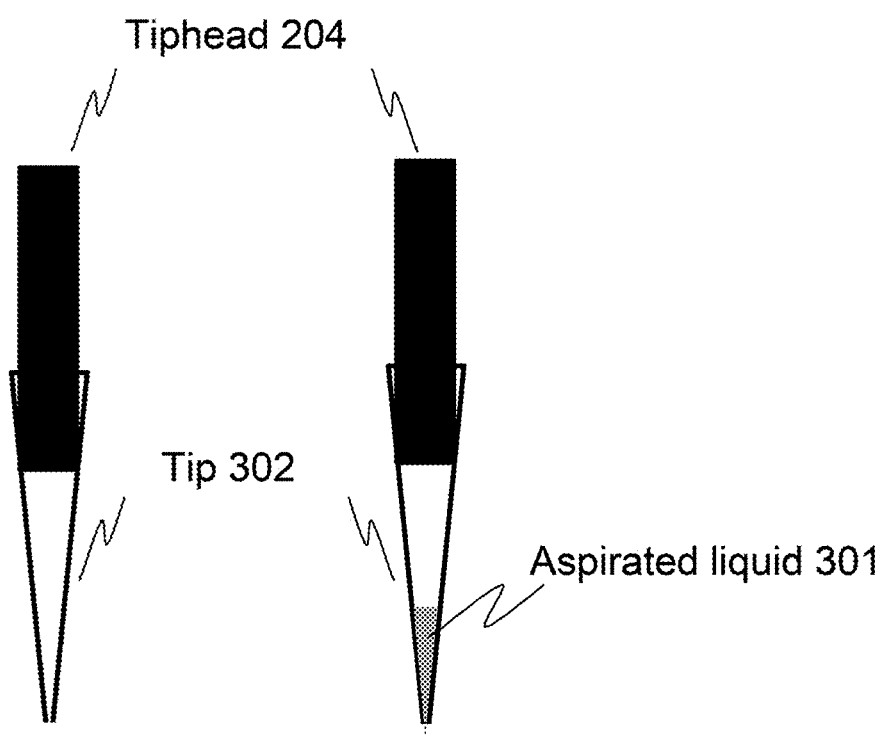
FIG. 11 illustrates chipheads and chips.

A detailed configuration of the sample preparation unit is shown in FIGS. 8 and 9. The sample preparation unit aims to prepare respective fractions to be analyzed automatically as described in embodiments 1-2. Respective components will be described in connection with the flow chart described later.

FIG. 10 is a flow chart of operations of the automatic measuring apparatus. The flow chart of FIG. 10 is merely an example and the operations may be different from this when a timing of the drug administration is different as described in embodiment 1, <step 2>. In this embodiment, plates having a plurality of cell holding regions (wells) are used as an example for illustrating the containers for holding cells, but the containers are not limited to plates and any containers that can contain cells may be, needless to say, used.

<Transfer from Culture Unit to Sample Preparation Unit>

Figure 7:
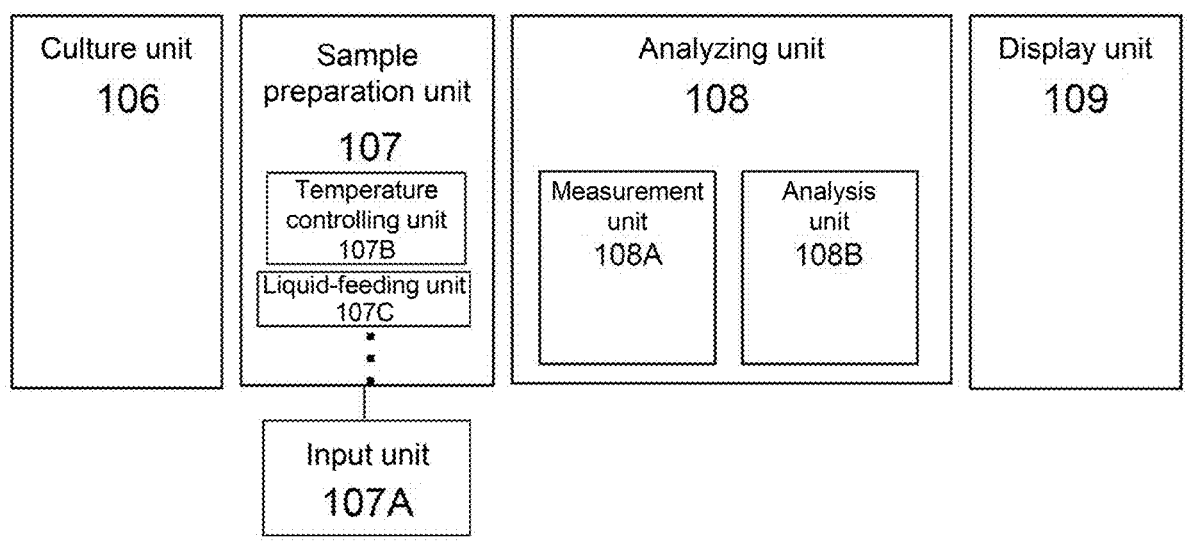
FIG. 7 illustrates a configuration of an automatic measuring apparatus.

Hepatocytes are first cultured in the culture unit 106 (FIGS. 7 and 10) (FIG. 10(a) substep 1). Subsequently, the plates containing the cultured hepatocytes are transferred on a plate holder 210 having a first temperature controlling function and a plate holder (211) having a second temperature controlling function in the sample preparation unit (FIGS. 7 and 10) (FIG. 10(a), substep 2).

<Sample Preparation: Corresponding to Step 1 in Embodiments 1 and 2>

An aspiration head 205, equipped with an aspiration nozzle to aspirate liquid, installed in the liquid-feeding unit 107C moves to a well 002, filled with medium to be removed, in a culture plate 001 on the aforementioned plate holder and aspirates the medium from the well to remove the total amount (FIG. 10, substep 3). The removed medium is collected (discarded) in the waste liquid tank 206.

Next, a tip 302 for containing liquid 301 from a tip rack 207 storing a plurality of tips is attached onto a tiphead 204 installed to an aspiration nozzle. The tiphead moves to a room temperature drug solution rack 209 and aspirate a buffer (FIG. 10, substep 4). The tiphead moves to a target well and introduces the buffer (FIG. 10(a), substep 5) and then the tiphead moves to a dust box 214 and discards the tip. An exchangeable tip is used here to prevent contaminations, but the tip is not limited to this.

The absorption head moves to the well filled with the buffer and removes the buffer (FIG. 10(a), substep 6). The removed medium is collected and discarded in the waste liquid tank 206. This step is repeated twice in total (washing step) (FIG. 10(a), substep 7).

Next, a tip in the tip rack 207 is attached onto the tiphead 204, the tiphead moves to the room temperature drug solution rack 209, and aspirates the buffer (FIG. 9, substep 8). The tiphead moves to the target well and introduces the buffer and then the tiphead moves to the dust box 214 and discards the tip. The plate is allowed to stand at 37° C. for 10 minutes (conditioning) (FIG. 10(a), substep 9). Subsequently, the aspiration head 205 moves to the target well filled with the buffer and removes the total amount of the buffer (FIG. 9 (a), sub step 10).

<Sample Preparation: Corresponding to Step 2 in Embodiments 1 and 2>

A tip in the tip rack 207 is attached onto the tiphead 204, the tiphead moves to the room temperature drug solution rack 209, and aspirates the drug solution (FIG. 10(a), substep 11). The tiphead moves to the target well and introduces the drug solution (FIG. 10(a), substep 12) and then the tiphead 204 moves to the dust box 214 and discards the tip. The plate is allowed to stand at 37° C. for 30 minutes (FIG. 10(a), substep 12). Subsequently, the temperature of the plate holder 210 having the first temperature controlling function and the plate holder 211 having the second temperature controlling function, which are an example configuration of the container holding unit for holding containers, is changed from 37° C. to 4° C. (FIG. 10(a), substep 13), and then the aspiration head 205 moves to the well filled with the drug solution and removes a total amount of the drug solution (FIG. 10(a), substep 14). Although the temperature controlling unit in this embodiment is described as a plate folder having a temperature controlling function, the temperature controlling unit may be, needless to say, separated from the container holding unit.

<Sample Preparation: Corresponding to Step 3 in Embodiments 1 and 2>

A tip in the tip rack 207 is attached onto the tiphead 204, the tiphead moves to a refrigerated drug solution rack 208, and aspirates a buffer (FIG. 10(a), substep 15). A refrigerated drug solution is used to stop active biological phenomena such as the transporter activity, as described above. The refrigerated drug solution rack 208 aims to hold a drug solution, a buffer, and the like at a low temperature for the purpose. The tiphead moves to the target well and introduces the buffer (FIG. 10(a), substep 16) and then the tiphead 204 moves to the dust box 214 and discards the tip. The absorption head moves to the well filled with the buffer and removes the buffer (FIG. 10(a), substep 17). The removed medium is discarded in the waste liquid tank 206. This step is repeated three times in total (washing step) (FIG. 10(a), substep 18).

<Sample Preparation: Corresponding to Step 4 in Embodiments 1 and 2>

The temperature of the plate holder 210 having the first temperature controlling function and the plate holder 211 having the second temperature controlling function is changed from 4° C. to 37° C. (FIG. 10(a), substep 19), a tip in the tip rack 207 is attached onto the tiphead 204, and the tiphead moves to a refrigerated drug solution rack 208 and aspirate the buffer (FIG. 10(a), substep 20). The tiphead moves to the target well and introduces the buffer (FIG. 10(a), substep 21) and then the tiphead 204 moves to the dust box 214 and discards the tip. The plate is allowed to stand at 37° C. for 30 minutes (FIG. 10(a), substep 20). Subsequently, the temperature of the plate holder 210 having the first temperature controlling function and the plate holder 211 having the second temperature controlling function is changed from 37° C. to 4° C. (FIG. 10(a), substep 22), and then a tip in the tip rack 207 is attached onto the tiphead 204, the tiphead moves to the well filled with the buffer containing the drug, aspirates the buffer (supernatant) containing the drug, and dispenses it into collection plates for collection on the first plate holder 212 and the second plate holder 213 (collection) (FIG. 10(*a*), substep 23).

<Sample Preparation: Corresponding to Step 5 in Embodiments 1 and 2>

The temperature of the plate holder 210 having the first temperature controlling function is changed from 4° C. to 37° C. (FIG. 10(*a*), substep 24), a tip in the tip rack 207 is attached onto the tiphead 204, and the tiphead moves to the room temperature drug solution rack (209) and aspirates a buffer containing EGTA (FIG. 10(*a*), substep 24). The tip head moves to a well for sequence 1 on the first plate holder 212, the buffer containing EGTA is introduced (FIG. 10(*b*), substep 25), then the tiphead 204 moves to the dust box 214, and the tip is discarded. The plate is allowed to stand at 37° C. for 30 minutes (FIG. 10(*b*), substep 26).

A tip in the tip rack 207 is attached onto the tiphead 204, the tiphead moves to the room temperature drug solution rack 209, and aspirates the buffer (FIG. 10(*b*), substep 27). The tip head moves to a well for sequence 2 on the first plate holder 212, the buffer is introduced (FIG. 10(*b*), substep 28), then the tiphead 204 moves to the dust box 214, and the tip is discarded. The plate is allowed to stand at 37° C. for 30 minutes (FIG. 10(*b*), substep 28).

A tip in the tip rack 207 is attached onto the tiphead 204, the tiphead moves to the refrigerated drug solution rack 209, and aspirates the buffer (FIG. 10(*b*), substep 29).

The tip head moves to a well for sequence 3 on the second plate holder 213, the buffer is introduced (FIG. 10(*b*), substep 30), then the tiphead 204 moves to the dust box 214, and the tip is discarded. The plate is allowed to stand at 4° C. for 30 minutes (FIG. 10(*b*), sub step 30).

A tip in the tip rack 207 is attached onto the tiphead 204 and the tiphead moves to the well filled with an EGTA buffer containing the drug, aspirates the EGTA buffer (supernatant) containing the drug, and dispenses (collects) the buffer into a collection plate for collection on the first plate holder 212 (FIG. 10(*b*), substep 31).

A tip in the tip rack 207 is attached onto the tiphead 204 and the tiphead moves to the well filled with the buffer containing the drug, aspirates the buffer (supernatant) containing the drug, and dispenses (collects) the buffer into a collection plate for collection on the first plate holder 212 (FIG. 10(*b*), substep 32).

A tip in the tip rack 207 is attached onto the tiphead 204, the tiphead moves to the well filled with the EGTA buffer containing the drug, aspirates the buffer (supernatant) containing the drug, and dispenses (collects) the buffer into the collection plate for collection on the first plate holder 213 (FIG. 10(*b*), substep 33).

The temperatures of the plate holder 210 having the first temperature controlling function and the plate holder 211 having the second temperature controlling function are both changed to room temperature (FIG. 10(*b*), substep 34), a tip in the tip rack 207 is attached onto the tiphead 204, and the tiphead moves to the room temperature drug solution rack 209 and aspirates 1% TritonX-100 or pure water/methanol (FIG. 10(*b*), substep 35). The tip head moves to wells for sequences 1, 2, and 3 on the plate holder (210) having the first temperature controlling function and the plate holder 211 having the second temperature controlling function, and introduces 1% TritonX-100 or pure water/methanol (FIG. 10(*b*), substep 36), the tiphead 204 moves to the dust box 214, and the tip is discarded.

A tip in the tip rack 207 is attached onto the tiphead 204 and the tiphead moves to a well filled with the aforementioned reagent, aspirates the total amount of the cell suspension, and dispenses the suspension into the collection plates for collection on the first plate holder 212 and the second plate holder 213 (collection) (FIG. 10(*b*), substep 37).

The operations of the aforementioned apparatus have been described as the respective operations of sequences 1-3 in embodiments 1 and 2 are conducted in order. The steps may be conducted in sequence or the steps may be conducted in parallel.

<Transfer from Sample Preparation Unit to Measurement Unit>

The collected drug in the culture plate is transferred to the measurement unit (FIG. 10(*b*), substep 38). In the measurement unit, the measurement of the drug by a plate reader or LCMS is conducted (FIG. 10(*b*), sub step 39).

<Calculation of Distribution Ratio and Score and Display of Result by Analysis Unit>

The distribution ratio and the score of respective fractions are calculated based on the measurement results (FIG. 10(*b*), substep 40). Then, the resultant calculated values are displayed on a display unit (FIG. 10(*b*), sub step 41).

Examples of the foregoing configurations described in connection with embodiments 1-3 include, for example:

<Configuration 1>

A componential analyzer, comprising: a holding unit for holding a plurality of containers holding a predetermined cell; a temperature controlling unit for controlling temperatures in the plurality of containers; and an analyzing unit for measuring a component in the plurality of containers and analyzing the measured component, wherein the plurality of containers is at least a first container and a second container; the first container and the second container each contain a first buffer solution; the temperature controlling unit controls temperature in the first container and temperature in the second container so that the temperatures become different from each other; and wherein the analyzing unit measures: an amount of the component excreted from a cell in the first container to the first buffer solution in the first container and an amount of the component excreted from a cell in the second container to the first buffer solution in the second container, and the analyzing unit analyzes an amount of the component excreted via transporters in the cells.

<Configuration 2>

The componential analyzer according to Configuration 1, wherein the predetermined cell is s hepatocyte; the plurality of containers comprises at least a first container, a second container, and a third container; the third container contains a second buffer solution supplemented with a predetermined substance;

the temperature controlling unit controls a first temperature in the first container and in the third container and a second temperature in the second container so that the second temperature is lower than the first temperature; wherein the analyzing unit measures: an amount of the component excreted from the hepatocyte in the first container to the first buffer solution in the first container, an amount of the component excreted from the hepatocyte in the second container to the first buffer solution in the second container, and an amount of the component excreted from the hepatocyte in the third container to the second buffer solution in the third container, and the analyzing unit analyzes: an amount of the component excreted via the transporters in the hepatocyte, an amount of the component excreted via the bile canaliculus of the hepatocyte, and an amount of the component excreted via a route other than the transporter and the bile canaliculus of the hepatocyte.

<Configuration 2>

The componential analyzer according to Configuration 2, further comprising a liquid-feeding unit for supplying or collecting a liquid in the plurality of containers, wherein the liquid-feeding unit: supplies the plurality of containers with a component solution comprising the component, collects the component solution and then supplies the plurality of containers with a third buffer solution, and collects the third buffer solution and then supplies the first container and the second container with the first buffer solution and the third container with the second buffer solution; and wherein the analyzing unit measures an amount of the component excreted into the third buffer solution from the hepatocyte contained in either of the plurality of containers.

<Configuration 4>

The componential analyzer according to Configuration 3, wherein the third buffer solution and the first buffer solution are the same buffer solution.

<Configuration 5>

The componential analyzer according to Configuration 3, wherein the temperature controlling unit controls temperature in at least one container of the plurality of containers when the at least one container contains the third buffer solution to be lower than the first temperature.

<Configuration 6>

The componential analyzer according to Configuration 1, wherein the analyzing unit measures: an amount of the component remaining in the hepatocyte in the third container and an amount of the component remaining in the hepatocyte in at least one container of the first container and the second container, and the analyzing unit analyzes an amount of the component remaining in other than bile canaliculi of the hepatocyte.

<Configuration 7>

A drug component analyzer, comprising: a holding unit for holding a plurality of containers containing a hepatocyte having absorbed a drug; a liquid-feeding unit for supplying a liquid in the plurality of containers; a temperature controlling unit for controlling temperatures in the plurality of containers; and an analyzing unit for measuring an amount of the drug in the plurality of containers and analyzing the measured drug, wherein the plurality of containers comprises a first container, a second container, and a third container; wherein the liquid-feeding unit supplies the first container and the second container with a first buffer solution and the third container with a second buffer solution promoting excretion of the drug from a bile canaliculus of the hepatocyte; the temperature controlling unit controls a temperature in the first container and in the third container and a temperature in the second container so that the later temperature is lower than the former temperature; wherein the analyzing unit analyzes each of: an amount of the drug excreted into the first buffer solution from the hepatocyte in the first container, an amount of the drug excreted into the first buffer solution from the hepatocyte in the second container, an amount of the drug excreted into the second buffer solution from the hepatocyte in the third container, an amount of the drug excreted via transporters in the hepatocyte, an amount of the drug excreted via bile canaliculi of the hepatocyte, and an amount of the component excreted via a route other than the transporter and the bile canaliculus of the hepatocyte.

<Configuration 8>

A drug component analyzer, comprising: a holding unit for holding a plurality of containers containing a hepatocyte having absorbed a drug; a liquid-feeding unit for supplying and discharging a liquid in the plurality of containers; a temperature controlling unit for controlling temperatures in the plurality of containers; and an analyzing unit for measuring an amount of the drug in the plurality of containers and analyzing the measured drug, wherein the liquid-feeding unit: supplies the drug to the plurality of containers, discharges the drug from the plurality of containers, supplies a pretreatment buffer solution, collects the pretreatment buffer solution from the plurality of containers and then supplies the first container and the second container of the plurality of culture containers with a first buffer solution, and the third container with a second buffer solution promoting excretion of the drug from a bile canaliculus of the hepatocyte; the temperature controlling unit controls a first temperature in the first container and in the third container and a second temperature in the second container so that the second temperature is lower than the first temperature;

wherein the analyzing unit analyzes each of: an amount of the drug excreted into the pretreatment buffer solution from the hepatocytes in the plurality of containers, an amount of the drug excreted into the first buffer solution from the hepatocyte in the first container, an amount of the drug excreted into the first buffer solution from the hepatocyte in the second container, an amount of the drug excreted into the second buffer solution from the hepatocyte in the third container, an amount of the drug excreted from the hepatocyte during pretreatment of the hepatocytes, an amount of the drug excreted via transporters in the hepatocyte, an amount of the drug excreted via bile canaliculi of the hepatocyte, and an amount of the drug excreted via a route other than the transporter and the bile canaliculus of the hepatocyte.

<Configuration 9>

The drug component analyzer according to Configuration 8, wherein the pretreatment buffer solution and the first buffer solution are the same buffer solution.

<Configuration 10>

The drug component analyzer according to Configuration 8, wherein the temperature controlling unit controls temperature in at least one container of the plurality of containers when the at least one container contains the pretreatment buffer solution to be lower than the first temperature.

<Configuration 11>

The drug component analyzer according to any one of Configurations 7 to 10, wherein the analyzing unit measures: an amount of the component remaining in the hepatocyte in the third container and an amount of the component remaining in the hepatocyte in at least one container of the first container and the second container, and the analyzing unit analyzes an amount of the component remaining in other than bile canaliculi of the hepatocyte.

<Configuration 12>

A method of componential analysis, comprising: a temperature controlling step of controlling temperatures in a first container containing a predetermined cell and in a second container containing the predetermined cell so that the temperature in the second container is lower than the temperature in the first container; a measuring step of measuring an amount of a component excreted from the cell in the first container to the first buffer solution in the first container and an amount of the component excreted from the cell in the second container to the first buffer solution in the second container; and an analyzing step of analyzing an amount of the component excreted via transporters in the cells based on the result measured in the measuring step.

<Configuration 13>

The method of componential analysis according to Configuration 12, wherein the cell is a hepatocyte; the third container containing the hepatocyte comprises a second buffer solution supplemented with a predetermined substance; the temperature controlling step comprises controlling a first temperature in the first container and in the third container and a second temperature in the second container so that the second temperature is lower than the first temperature; the measuring step comprises measuring the followings: an amount of the component excreted from the hepatocyte in the first container to the first buffer solution in the first container, an amount of the component excreted from the hepatocyte in the second container to the first buffer solution in the second container, and an amount of the component excreted from the hepatocyte in the third container to the second buffer solution in the third container; and the analyzing step comprises analyzing each of the followings: an amount of the component excreted via the transporters in the hepatocyte, an amount of the component excreted via the bile canaliculus of the hepatocyte, and an amount of the component excreted via a route other than the transporter and the bile canaliculus of the hepatocyte.

<Configuration 14>

The method of componential analysis according to Configuration 13, further comprising: prior to the temperature controlling step, a liquid-feeding step of supplying or collecting a liquid in a plurality of containers comprising at least the first container, the second container, and the third container; wherein the liquid-feeding step comprises: supplying the plurality of containers with a component solution comprising the component, collecting the component solution and then supplying the plurality of containers with a third buffer solution, and collecting the third buffer solution and then supplying the first container and the second container with the first buffer solution and the third container with the second buffer solution; and the measuring step comprises analyzing an amount of the component excreted into the third buffer solution from the hepatocyte contained in at least one of the plurality of containers.

<Configuration 15>

The method of componential analysis according to Configuration 14, wherein the third buffer solution and the first buffer solution are the same buffer solution.

<Configuration 16>

The method of componential analysis according to Configuration 14, further comprising: prior to the temperature controlling step, a pretreatment temperature controlling step of controlling a temperature in at least one container of the plurality of containers when the at least one container contains the third buffer solution to be lower than the first temperature.

<Configuration 17>

A method of analyzing a drug component, comprising: a liquid-feeding step of supplying a liquid to a plurality of containers containing a hepatocyte having absorbed a drug; a temperature controlling step of controlling temperatures in the plurality of containers; a measuring step of measuring an amount of the drug in the plurality of containers; and an analyzing step of analyzing the drug measured in the measuring step, wherein the plurality of containers comprises a first container, a second container, and a third container; the liquid-feeding step comprises supplying the first container and the second container with a first buffer solution and the third container with a second buffer solution promoting excretion of the drug from a bile canaliculus of the hepatocyte; the temperature controlling step comprises controlling a temperature in the first container and in the third container and a temperature in the second container so that the later temperature is lower than the former temperature; and the measuring step comprises measuring the followings: an amount of the drug excreted into the first buffer solution from the hepatocyte in the first container, an amount of the drug excreted into the first buffer solution from the hepatocyte in the second container, an amount of the drug excreted into the second buffer solution from the hepatocyte in the third container, an amount of the component remaining in the hepatocyte in the third container and an amount of the component remaining in the hepatocyte in at least one container of the first container and the second container; and the analyzing step comprises analyzing each of the followings: an amount of the drug excreted via transporters in the hepatocytes, an amount of the drug excreted via bile canaliculi of the hepatocytes, an amount of the drug excreted via a route other than the transporter and the bile canaliculus of the hepatocyte, and an amount of the component remaining in other than the bile canaliculus of the hepatocyte.

<Configuration 18>

A method of analyzing a drug component, comprising: a liquid-feeding step of supplying or discharging a liquid in a plurality of containers containing a hepatocyte having absorbed a drug; a temperature controlling step of controlling temperatures in the plurality of containers; a measuring step of measuring an amount of the drug in the plurality of containers; and an analyzing step of analyzing the drug measured in the measuring step, wherein the liquid-feeding step comprises: supplying the drug to the plurality of containers, discharging the drug from the plurality of containers and supplying a pretreatment buffer solution, collecting the pretreatment buffer solution from the plurality of containers and then supplying the first container and the second container of the plurality of culture containers with a first buffer solution, and the third container with a second buffer solution promoting excretion of the drug from a bile canaliculus of the hepatocyte; the temperature controlling step comprises controlling a first temperature in the first container and in the third container and a second temperature in the second container so that the second temperature is lower than the first temperature; the measuring step comprises measuring the followings: an amount of the drug excreted into the pretreatment buffer solution from the hepatocytes in the plurality of containers, an amount of the drug excreted into the first buffer solution from the hepatocyte in the first container, an amount of the drug excreted into the first buffer solution from the hepatocyte in the second container, an amount of the drug excreted into the second buffer solution from the hepatocyte in the third container, an amount of the component remaining in the hepatocyte in the third container and an amount of the component remaining in the hepatocyte in at least one container of the first container and the second container; and the analyzing step comprises analyzing each of the followings: an amount of the drug excreted from the hepatocytes during pretreatment of the hepatocytes, an amount of the drug excreted via transporters in the hepatocytes, an amount of the drug excreted via bile canaliculi of the hepatocytes, an amount of the drug excreted via a route other than the transporter and the bile canaliculus of the hepatocyte, and an amount of the component remaining in other than the bile canaliculus of the hepatocyte.

<Configuration 19>

The method of componential analysis according to Configuration 18, wherein the pretreatment buffer solution and the first buffer solution are the same buffer solution.

<Configuration 20>

The method of analyzing a drug component according to Configuration 18 comprising: prior to the temperature controlling step, a pretreatment temperature controlling step of controlling a temperature in at least one container of the plurality of containers when the at least one container contains the pretreatment buffer solution to be lower than the first temperature.

We claim:

1. A componential analysis method for evaluating an amount of a chemical substance which is taken up into a cell or excreted from a cell, the method comprising:
   a first step of adding a first buffer solution to a first container and a second container each comprising a cell containing a chemical substance to be evaluated, adjusting a temperature within the first container and the second container to a first temperature and incubating, and adjusting the temperature within the first container and the second container to a second temperature which is lower than the first temperature;
   a second step of collecting the first buffer solution from each of the first container and the second container;
   a third step of adding a second buffer solution comprising a reagent for removing cell-cell adhesion to the first container after the second step, and adjusting the temperature within the first container to a third temperature and incubating;
   a fourth step of adding a third buffer solution to the second container after the second step, and adjusting the temperature within the second container to the third temperature and incubating;
   a first determination step of determining an amount S of the chemical substance which is excreted from the cell to the first buffer solution in the first container and/or the second container after the first step;
   a second determination step of determining an amount B1 of the chemical substance which is excreted from the cell to the second buffer solution in the first container after the third step;
   a third determination step of determining an amount B2 of the chemical substance which is excreted from the cell to the third buffer solution in the second container after the fourth step; and
   evaluating an amount of the chemical substance excreted from a basal/basolateral side of the cell based on the amount S of the chemical substance.

2. The componential analysis method of claim 1, wherein the method comprises:
   evaluating the amount of the chemical substance excreted from an apical side of the cell based on the amount B1 and the amount B2 of the chemical substance.

3. A componential analysis method for evaluating an amount of a chemical substance which is taken up into a cell or excreted from a cell, the method comprising:
   a first step of adding a first buffer solution to a first container and a second container each comprising a cell containing a chemical substance to be evaluated, adjusting a temperature within the first container and the second container to a first temperature and incubating, and adjusting the temperature within the first container and the second container to a second temperature which is lower than the first temperature;
   a second step of collecting the first buffer solution from each of the first container and the second container;
   a third step of adding a second buffer solution to the first container after the second step, and adjusting the temperature within the first container to a third temperature and incubating;
   a fourth step of adding the second buffer solution to the second container after the second step, and adjusting the temperature within the second container to a fourth temperature which is lower than the third temperature and incubating;
   a first determination step of determining an amount B2 of the chemical substance which is excreted from the cell to the second buffer solution in the first container after the third step; and
   a second determination step of determining an amount B3 of the chemical substance which is excreted from the cell to the second buffer solution in the second container after the fourth step.

4. The componential analysis method of claim 3, wherein the method comprises:
   a third determination step of determining an amount S of the chemical substance which is excreted from the cell to the first buffer solution in the first container and/or the second container after the first step; and
   evaluating an amount of the chemical substance excreted from a basal/basolateral side of the cell based on the amount S of the chemical substance.

5. The componential analysis method of claim 3, wherein the method comprises:
   evaluating an amount of the chemical substance excreted from a basal/basolateral side of the cell by diffusion based on the amount B3 of the chemical substance; and
   evaluating the amount of the chemical substance excreted from the basal/basolateral side of the cell via transporters based on the amount B2 and the amount B3 of the chemical substance.

6. A componential analysis method for evaluating an amount of a chemical substance which is taken up into a cell or excreted from a cell, the method comprising:
   a first step of adding a first buffer solution to a container which comprises a cell containing a chemical substance to be evaluated, adjusting a temperature within the container to a first temperature and incubating, and adjusting the temperature within the container to a second temperature which is lower than the first temperature;
   a second step of collecting the first buffer solution from the container after the first step;
   a third step of adding a second buffer solution to the container after the second step, and adjusting the temperature within the container to a third temperature and incubating;
   a first determination step of determining an amount S of the chemical substance which is excreted from the cell to the first buffer solution in the container after the first step;
   a second determination step of determining an amount B2 of the chemical substance which is excreted from the cell to the second buffer solution in the container after the third step; and
   evaluating an amount of the chemical substance excreted from a basal/basolateral side of the cell based on the amount S of the chemical substance.

7. The componential analysis method of claim 6, wherein the method comprises:
   evaluating the amount of the chemical substance excreted from the basal/basolateral side of the cell based on the amount B2 of the chemical substance.

8. A componential analysis method for evaluating an amount of a chemical substance which is taken up into a cell or excreted from a cell, the method comprising:
   a first step of adding a first buffer solution to a first container, a second container and a third container each comprising a cell containing a chemical substance to be evaluated, adjusting a temperature within the first container, the second container and the third container to a first temperature and incubating, and adjusting the temperature within the first container, the second container and the third container to a second temperature which is lower than the first temperature;

a second step of collecting the first buffer solution from each of the first container, the second container and the third container;

a third step of adding a second buffer solution comprising a reagent for removing cell-cell adhesion to the first container after the second step, and adjusting the temperature within the first container to a third temperature and incubating;

a fourth step of adding a third buffer solution to the second container after the second step, and adjusting the temperature within the second container to the third temperature and incubating;

a fifth step of adding the third buffer solution to the third container after the second step, and adjusting the temperature within the third container to a fourth temperature which is lower than the third temperature and incubating;

a first determination step of determining an amount B1 of the chemical substance which is excreted from the cell to the second buffer solution in the first container after the third step;

a second determination step of determining an amount B2 of the chemical substance which is excreted from the cell to the third buffer solution in the second container after the fourth step; and a third determination step of determining an amount B3 of the chemical substance which is excreted from the cell to the third buffer solution in the third container after the fifth step.

9. The componental analysis method of claim 8, wherein the method comprises:

a fourth determination step of determining an amount S of the chemical substance which is excreted from the cell to the first buffer solution in at least one of the first container, the second container, and the third container after the first step; and evaluating an amount of the chemical substance excreted from a basal/basolateral side of the cell based on the amount S of the chemical substance.

10. The componental analysis method of claim 8, wherein the method comprises:

evaluating an amount of the chemical substance excreted from an apical side of the cell based on the amount B1 and the amount B2 of the chemical substance;

evaluating an amount of the chemical substance excreted from a basal/basolateral side of the cell by diffusion based on the amount B3 of the chemical substance; and evaluating the amount of the chemical substance excreted from the basal/basolateral side of the cell via transporters based on the amount B2 and the amount B3 of the chemical substance.

11. A componental analysis method for evaluating an amount of a chemical substance which is taken up into a cell or excreted from a cell, the method comprising:

a first step of adding a first buffer solution to a first container, a second container, a third container and a fourth container each comprising a cell containing a chemical substance to be evaluated, adjusting a temperature within the first container, the second container, the third container and the fourth container to a first temperature and incubating, and adjusting the temperature within the first container, the second container, the third container and the fourth container to a second temperature which is lower than the first temperature;

a second step of collecting the first buffer solution from each of the first container, the second container, the third container and the fourth container;

a third step of adding a second buffer solution comprising a reagent for removing cell-cell adhesion to the first container after the second step, and adjusting the temperature within the first container to a third temperature and incubating;

a fourth step of adding a third buffer solution to the second container after the second step, and adjusting the temperature within the second container to the third temperature and incubating;

a fifth step of adding the third buffer solution to the third container after the second step, and adjusting the temperature within the third container to a fourth temperature which is lower than the third temperature and incubating;

a sixth step of adding the second buffer solution comprising a reagent for removing cell-cell adhesion to the fourth container after the second step, and adjusting the temperature within the fourth container to the fourth temperature which is lower than the third temperature and incubating;

a first determination step of determining an amount B1 of the chemical substance which is excreted from the cell to the second buffer solution in the first container after the third step;

a second determination step of determining an amount B2 of the chemical substance which is excreted from the cell to the third buffer solution in the second container after the fourth step;

a third determination step of determining an amount B3 of the chemical substance which is excreted from the cell to the third buffer solution in the third container after the fifth step; and a fourth determination step of determining an amount B4 of the chemical substance which is excreted from the cell to the second buffer solution in the fourth container after the sixth step.

12. The componental analysis method of claim 11, wherein the method comprises:

a fifth determination step of determining an amount S of the chemical substance which is excreted from the cell to the first buffer solution in at least one of the first container, the second container, the third container, and the fourth container after the first step; and evaluating an amount of the chemical substance excreted from a basal/basolateral side of the cell based on the amount S of the chemical substance.

13. The componental analysis method of claim 11, wherein the method comprises:

evaluating an amount of the chemical substance excreted from a basal/basolateral side of the cell by diffusion based on the amount B3 of the chemical substance;

evaluating the amount of the chemical substance excreted from the basal/basolateral side of the cell via transporters based on the amount B2 and the amount B3 of the chemical substance;

evaluating an amount of the chemical substance excreted from an apical side of the cell by diffusion based on the amount B3 and the amount B4 of the chemical substance; and evaluating the amount of the chemical substance excreted from the apical side of the cell via transporters based on the amount B1, the amount B2, the amount B3 and the amount B4 of the chemical substance.

\* \* \* \* \*